United States Patent

Van Tassel et al.

[11] Patent Number: 5,728,132
[45] Date of Patent: Mar. 17, 1998

[54] SELF-SEALING VASCULAR ACCESS DEVICE

[75] Inventors: Robert A. Van Tassel, Excelsior; David R. Holmes; Robert S. Schwartz, both of Rochester, all of Minn.

[73] Assignee: Tricardia, L.L.C., Excelsior, Minn.

[21] Appl. No.: 629,022

[22] Filed: Apr. 8, 1996

[51] Int. Cl.$^6$ .................................................. A61B 17/04
[52] U.S. Cl. .................................................. 606/213; 606/191
[58] Field of Search .................................. 604/65–67, 38, 604/41, 51, 53, 96; 606/213, 1, 108, 192, 185, 190; 128/748, 691

[56] References Cited

U.S. PATENT DOCUMENTS

| | | |
|---|---|---|
| 4,531,943 | 7/1985 | Van Tassel et al. . |
| 4,738,658 | 4/1988 | Magro et al. . |
| 4,744,364 | 5/1988 | Kensey . |
| 4,838,280 | 6/1989 | Haaga . |
| 4,852,568 | 8/1989 | Kensey . |
| 4,890,612 | 1/1990 | Kensey . |
| 5,021,059 | 6/1991 | Kensey et al. . |
| 5,041,129 | 8/1991 | Hayhurst et al. . |
| 5,129,882 | 7/1992 | Weldon et al. . |
| 5,192,300 | 3/1993 | Fowler . |
| 5,197,971 | 3/1993 | Bonutti .......................... 606/192 |
| 5,221,259 | 6/1993 | Weldon et al. . |
| 5,222,974 | 6/1993 | Kensey et al. . |
| 5,281,197 | 1/1994 | Arias et al. . |
| 5,290,310 | 3/1994 | Makower et al. . |
| 5,324,306 | 6/1994 | Makower et al. . |
| 5,419,765 | 5/1995 | Weldon et al. ................. 606/213 |
| 5,447,502 | 9/1995 | Haaga . |
| 5,486,195 | 1/1996 | Myers et al. .................... 606/213 |
| 5,496,332 | 3/1996 | Sierra et al. .................... 606/213 |

FOREIGN PATENT DOCUMENTS

04761784A1 3/1992 European Pat. Off. .

*Primary Examiner*—Guy V. Tucker
*Assistant Examiner*—Patrick W. Rasche
*Attorney, Agent, or Firm*—Haugen and Nikolai, P.A.

[57] ABSTRACT

An instrument for achieving rapid hemostasis at the conclusion of a catheterization procedure comprises a device for injecting a fluid hemostatic agent into a puncture wound that is operatively associated with a conventional introducer sheath component of the introducer used to gain access to a blood vessel using the Seldinger technique. The hemostatic agent injection device includes a tubular member that can be concentrically disposed with a tubular introducer sheath so as to be slidable therealong and where the injection device includes a hemostatic agent inlet port at a proximal end thereof and an ejection port at a distal end, the two ports being interconnected by a lumen. In a first embodiment, the hemostatic agent injection device is adapted to coaxially surround the introducer sheath and in an alternate embodiment, the injection device is coaxially disposed within the lumen of the introducer sheath.

19 Claims, 3 Drawing Sheets

SELF-SEALING VASCULAR ACCESS DEVICE

BACKGROUND OF THE INVENTION

I. Field of the Invention

This invention relates generally to a surgical device which is used to gain vascular access percutaneously to allow a variety of cardiac and vascular procedures to be performed, and more particularly to an instrument used as a part of a conventional catheter introducer for achieving rapid hemostasis following the completion of an intravascular procedure.

II. Discussion of the Prior Art

In a percutaneous intravascular procedure, such as when performing angioplasty or angiography, access to the vascular space is generally obtained using the so-called Seldinger technique where, first, a hollow needle is used to create a puncture wound through the skin, the underlying muscle tissue and through the wall of a selected blood vessel, such as the femoral artery. Next, a guidewire is inserted through the tubular needle until its distal end is located in the blood vessel, at which time the needle is stripped off of the guidewire and replaced with an introducer sheath and dilator. The introducer sheath typically will include a self-sealing hemostatic valve on its proximal end for sealing around the guidewire. The guidewire is then advanced into the vascular space through the introducer and directed to a preselected area of the vascular system. Once the guidewire is so positioned, a catheter is then advanced over the guidewire to the desired area.

Once the procedure has been completed and the catheter and the introducer sheath are removed from the puncture site, there may be profuse bleeding, especially when the patient has been on anticoagulant therapy such as Heparin, Coumadin, aspirin or thrombolytic agents. Manual pressure must then be applied for a prolonged period of time to obtain hemostasis. So as to not unduly tie up trained medical personnel, an external vascular clamp, sandbags or a pressure dressing may be used to apply pressure to the puncture site to help insure satisfactory, permanent hemostasis.

The medical literature has addressed the problem of achieving hemostasis following removal of a percutaneously applied intravascular introducer in such uses as angiography or angioplasty. The Makower et al. U.S. Pat. No. 5,290,310 describes a device for delivering a hemostatic substance subcutaneously against a penetration site in a wall of a blood vessel. An instrument containing a toroidal-shaped collagen plug within a barrel thereof is made to surround the exterior of a tubular introducer. The instrument includes a pusher mechanism for ejecting the collagen plug into the puncture wound and against the exterior wall of the blood vessel at the site of the puncture.

The Weldon et al. U.S. Pat. No. 5,129,882 also discloses a surgical implement for injecting a hemostatic agent in a puncture wound by routing the injection device through the lumen of the introducer sheath after it has been retracted sufficiently so that the distal end thereof is no longer in the blood vessel. Then by deploying a plunger, the hemostatic agent is forced out of the instrument and against the exterior wall of the artery proximate the puncture wound.

U.S. Pat. Nos. 4,744,364, 4,852,974, 4,890,612, 5,021,059 and 5,222,974, issued to Kenneth Kensey each describe a method and apparatus for effecting hemostasis by first inserting an anchoring device through the puncture wound and into the blood vessel while using a filament attached to the anchoring device to hold it in place as an appropriate sealant is injected into the wound. The anchoring device prevents entrance of the sealing material into the blood vessel and serves as an anchor and guide for addressing selected vessels.

Still other devices for injecting a hemostatic agent into a puncture wound following a vascular procedure include the Arias et al. U.S. Pat. No. 5,281,197, the Haaga U.S. Pat. No. 4,838,280, the Fowler U.S. Pat. No. 5,192,300, the Magro et al. U.S. Pat. No. 4,738,658 and published European Patent Application 0 476 178A1 of Bioplex Medical, B.V.

For the most part, the aforereferenced prior art patents describe devices that are intended to be used in combination with a tubular introducer sheath for deploying a hemostatic agent following withdrawal of any guidewire, guide catheter or working catheter at the conclusion of the procedure. Certain of those devices require significant skill in the use thereof to preclude potential complications occasioned by unwanted placement of the hemostatic agent within the blood vessel itself.

A need exists for a unitary combination of an introducer sheath, introducer dilator and a device for effecting hemostasis following a vascular procedure where the assembly is self-contained, is small in size so as not to interfere with the manipulation of the working catheter and catheter exchanges and requires minimal time and skill to utilize.

SUMMARY OF THE INVENTION

In accordance with a first embodiment of the invention, there is provided a device for sealing percutaneous punctures in a blood vessel that comprises an elongated, tubular member having a proximal end, a distal end and a working lumen extending therebetween. The elongated tubular member includes an injection lumen leading to at least one injection outlet port formed through the side wall of the tubular member proximate the distal end thereof. Affixed to the proximal end of the elongated, tubular member is a hub having an injection inlet port that is in fluid communication with the injection lumen and which includes a bore that is aligned with the working lumen of the elongated tubular member. The bore and the working lumen are dimensioned to receive a tubular introducer sheath therethrough with the tubular introducer being slidable relative to the elongated tubular member of the injection device. The elongated tubular member and the tubular introducer sheath are assembled together along with a dilator at the factory and packaged as a unit. When the device is being used in carrying out vascular access using the Seldinger technique, the puncture sealing device is retracted in the proximal direction, such that the introducer sheath portion may be used with a dilator in a conventional way. Following the conclusion of the catheterization procedure, the puncture sealing device can be advanced in the distal direction along the outer surface of the introducer sheath as a guide until the elongated tubular member abuts the exterior wall of the blood vessel. Now, a suitable hemostatic agent can be injected by means of a syringe into the injection inlet port in the hub and allowed to flow through the injection lumen and out through the injection outlet port to deposit a predetermined quantity of the hemostatic agent into the wound where it remains following removal of the introducer sheath itself.

In accordance with a further embodiment of the invention, the device for injecting the hemostatic agent comprises an obturator sized to slide within the lumen of a tubular introducer or sheath where the obturator includes a lumen extending toward but short of a closed distal end. Communicating with the lumen is an outlet port in a side wall of the obturator. At the conclusion of the catheterization procedure, the obturator is inserted through the lumen of the tubular introducer sheath until it is sensed that the distally located outlet port has found its way into the blood vessel through the puncture to be sealed. The tubular introducer sheath is then retracted in the proximal direction as the obturator is held fixed until only the obturator remains within the puncture wound. It, too, is then retracted to the point where its outlet port is no longer in the blood vessel. A hemostatic agent is then injected through the lumen of the obturator and out the outlet port in the side wall, hemostaticly sealing the wound.

By incorporating an inflatable balloon proximate the distal tip of the obturator at a location that is slightly distal of the outlet port, upon inflation of the balloon, none of the fluid hemostatic agent can flow beyond the balloon into the blood vessel.

DESCRIPTION OF THE DRAWINGS

The foregoing features, objects and advantages of the invention will become apparent to those skilled in the art from the following detailed description of the preferred embodiments, especially when considered in conjunction with the accompanying drawings in which.

DESCRIPTION OF THE PREFERRED EMBODIMENT

Figure 1:
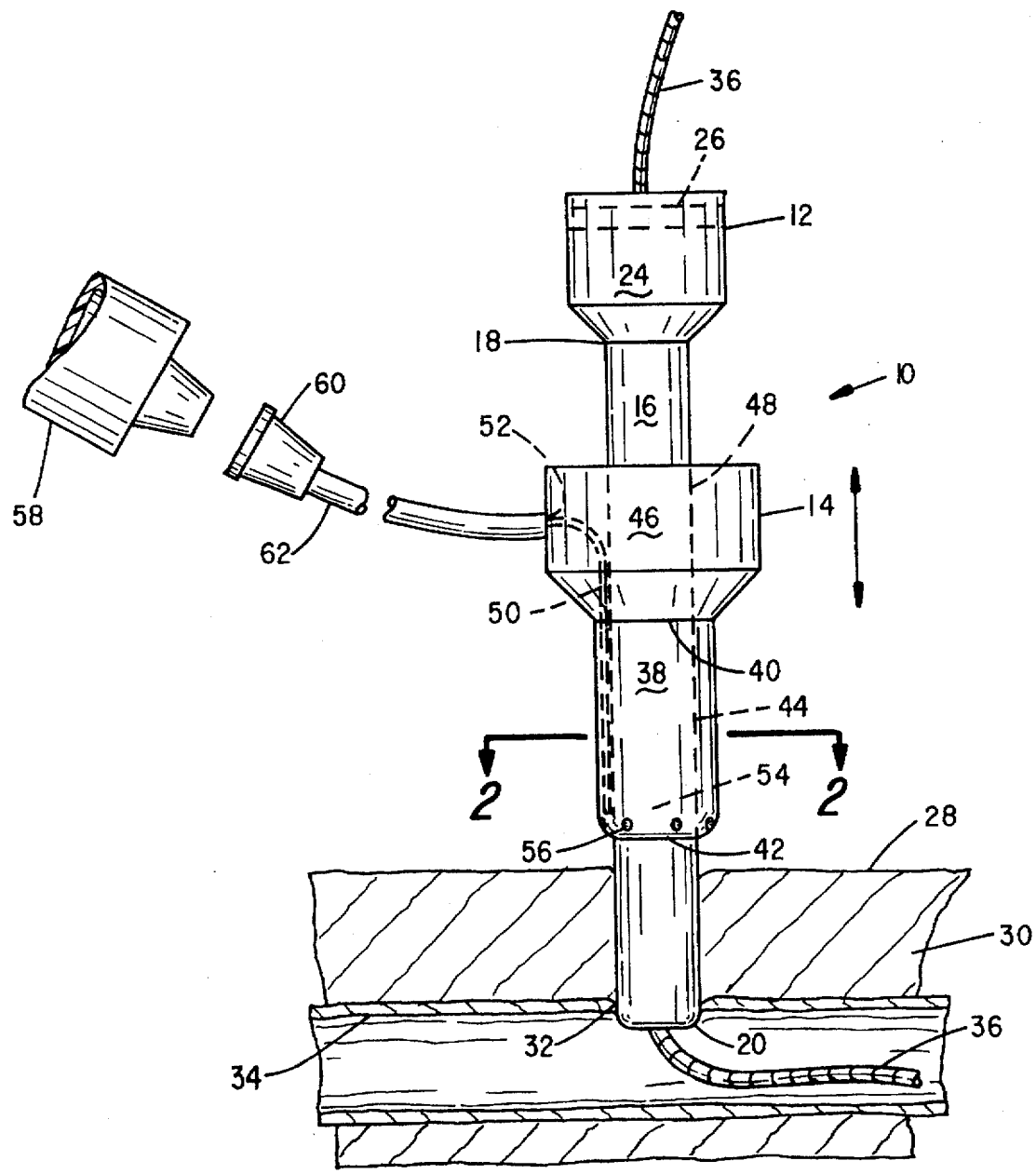
FIG. 1 is a side elevational view of a first embodiment of the invention.
Figure 2:
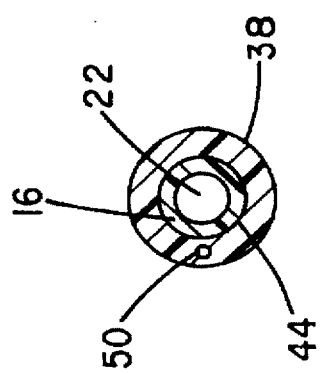
FIG. 2 is a cross sectional view taken along the line 2—2 in FIG. 1.

Referring to FIG. 1, there is indicated generally by numeral 10 a device for sealing percutaneous punctures in a blood vessel. It is seen to comprise a two-piece assembly of a conventional catheter introducer sheath 12 and a hemostatic agent injection device 14 that closely surrounds the introducer sheath 12. The introducer sheath, itself, comprises an elongated tubular body 16 having a proximal end 18, a distal end 20 and a lumen 22 (FIG. 2) extending therebetween. Integrally molded or otherwise affixed to the proximal end 18 of the tubular body 16 is a hub 24 that contains a hemostatic seal 26. The seal typically comprises one or more elastomeric disks having self-closing slits formed through the thickness dimension thereof and which cooperate with a guidewire, a catheter body or similar instrument that may be fed through the introducer to block the backflow of blood out through the proximal end of the introducer sheath.

As depicted in FIG. 1, the distal end 20 of the tubular member 16 is shown as penetrating through the skin 28 underlying layers of flesh 30 and through a puncture wound 32 created in a wall 34 of a blood vessel such as an artery. The figure also shows a segment of a conventional guidewire 36 extending through the introducer sheath 12 and into the blood vessel 34.

The hemostatic agent injection device 14 comprises a molded plastic article. It has an elongated tubular member 38 with a proximal end 40 and a distal end 42. The length of the tubular member 38 is substantially less than the length of the tubular portion 16 of the introducer 12 and it includes a lumen 44 (FIG. 2) whose diameter is slightly larger than the outer diameter of the tubular portion 16 of the introducer sheath 12, such that the device 14 is able to be reciprocally slid along the tubular portion 16 of the introducer sheath.

Integrally molded with or otherwise affixed to the proximal end 40 of the hemostatic agent injection device 14 is an enlarged hub member 46 that can readily be grasped by a physician. The hub member 46 includes a longitudinal bore 48 that is aligned with the bore defining the lumen 44. A further, generally parallel, bore 50 extends longitudinally through the wall of the tubular member 38 from an injection inlet port 52 formed in the hub 46 and leading to an annular chamber 54 near the proximal end 42 of the tubular member 38. Formed through the outside wall of the chamber 54 are a plurality of apertures as at 56.

A syringe 58 or other type of pump for dispensing a fluid hemostatic agent may be coupled, via a Luer fitting 60 and tubing 62, to the inlet port 52 on the hub 46. By depressing the plunger or piston of the syringe, the hemostatic agent is made to flow through the lumen 50 into the chamber 54 where it ultimately exudes out of the apertures 56 of the injection device 14.

In use, toward the termination of the catheterization procedure, any working catheters, guide catheters and the guidewire 36 will be stripped out of the proximal end of the introducer sheath 12 with the introducer remaining in place. Next, the physician will slide the injection device 14 down the tubular barrel 16 of the introducer causing the distal end 42 of the injection device to penetrate through the skin and musculature until reaching the vessel wall 34. Because of the texture of the various tissue levels encountered, and because of the manner in which the distal end of the injection device is configured, the physician will be aware of the proximity of the injector device to the outer wall of the blood vessel.

Figure 3:
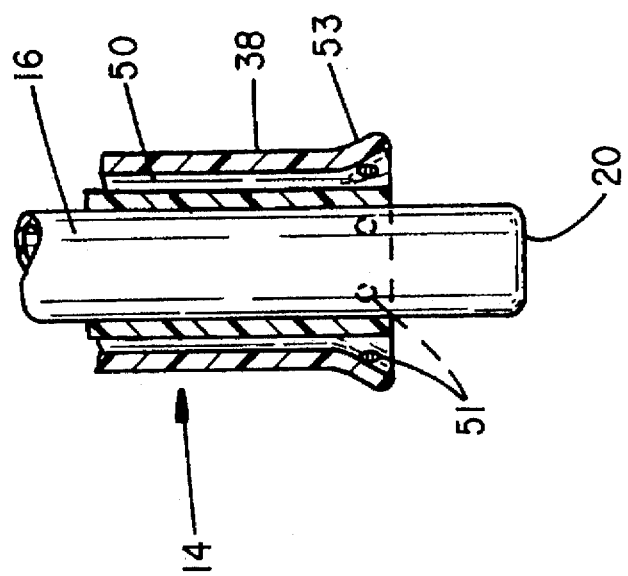
FIG. 3 is a sectioned partial view of the assembly of FIG. 1 in accordance with a further configuration.

To enhance the tactile response upon engagement of the distal end 42 of the injection device 14 with the wall of the blood vessel 34, the distal end 42 can be outwardly flared as is illustrated in FIG. 3. FIG. 3 illustrates a cross-section view showing an annular injection lumen 50 effectively formed between double walls of the tubular member 38 and the annular lumen leads to a plurality of outlet apertures as at 51, which are regularly angularly spaced around the periphery of the flared portion 53 of tubular member 38. Irrespective of the tip configuration on the injection device 14, and continuing with the description of the use of the instrument, the physician will actuate the plunger of the syringe 58 to inject the clotting agent into the wound at the site of entrance through the selected vessel. The introducer will then be removed. The relatively high arterial pressure and the snug fit of an obturator or introducer at the entrance site of the vessel will minimize the inadvertent entry of the hemostatic material into the blood vessel 34.

The fluid hemostatic agent employed in carrying out the present invention may be a clotting agent, such as thrombin, fibrin, fibrin glue or a collagen slurry or gel. It may also comprise a tissue adhesive, such as methacrylates, or cynaocrylates. Vasoconstrictive drugs, such as phenylephrine, norepinephrine, epinephrine, prostaglandin F2 alpha, endothelin, methergine, oxytocin and isoprel may also be useful in stemming blood flow. Other astringent substances, such as ferric chloride, zinc oxide, permaganates, or tannic acid can be appropriately formulated with fillers, binders or matrix materials so as to be of sufficiently law viscosity to permit introduction, via injection through the hemostatic agent injection device 14.

ALTERNATIVE EMBODIMENT

Figures 4, 5:
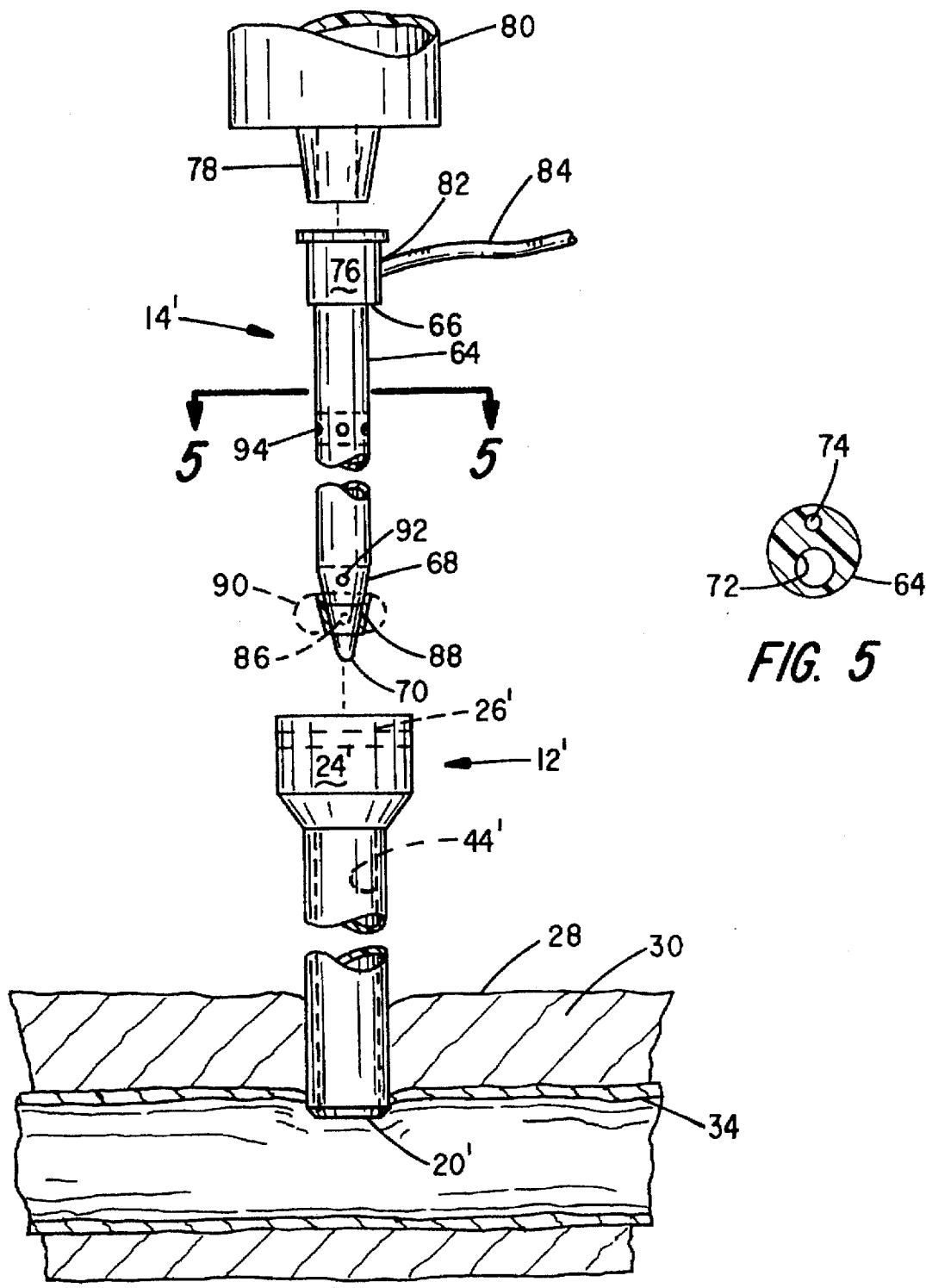
FIG. 4 is an exploded side elevational view of a further embodiment of the present invention.
FIG. 5 is a cross sectional view taken along the line 5—5 in FIG. 4.

FIG. 4 illustrates an alternative embodiment of the present invention. It again includes a conventional vascular introducer sheath 12', similar in its construction to the vascular introducer sheath 12 of FIG. 1. As such, it includes a hub 24' containing an elastomeric seal 26' precluding backflow of blood. The distal end of the introducer sheath 12' is again illustrated as being disposed in a puncture wound formed in the skin 28 and musculature 30 and a blood vessel wall 34.

The hemostatic agent injection device indicated generally by numeral 14' comprises an obturator 64 having a proximal end 66 and a tapered distal portion 68 terminating in a closed end 70.

As shown in the cross-sectional view of FIG. 5, the obturator 64 is generally cylindrical and includes an injection lumen 72 and an inflation lumen 74 extending longitudinally from the proximal end 66 down to the distal end portion 68 thereof. The outside diameter of the obturator 64 is sized so as to permit it to be passed through the bore 44' forming the lumen of the tubular introducer sheath 12'.

Affixed to the proximal end 66 of the injection device 14' is an integrally molded hub member 76, which preferably comprises a Luer-type fitting for receiving a tapered nose 78 of a syringe or other type of pump 80. The injection lumen 72 is thus in fluid communication with the interior of the syringe 80.

In accordance with an optional feature of the instant embodiment, an inflatable balloon 90 may be bonded to the outer wall of the obturator 64 near its distal end. If such a balloon is to be used, an inflation input port 82 may be formed in the side wall of the hub 76 and which may be connected by tubing 84 to a suitable source of inflation fluid (not shown). The inflation input port 82 will be in fluid communication with the inflation lumen 74 extending through the tubular body of the obturator 64. Formed close to, but short of, the closed end 70 of the obturator will be an inflation outlet port 86. It may then be overlaid by a thin, elastic, elastomeric band 88, which would be bonded at its opposed edges to the exterior surface of the obturator body. When an injection fluid under pressure is injected through the tubing 84 and down the inflation lumen 74, the elastomeric band inflates to create a balloon member as indicated by the dotted lines 90 in FIG. 4.

A position sensing port 92 is located a predetermined distance proximal of the closed end 70 of the obturator and where the device is designed to incorporate a retention balloon, the position sensing port is located immediately proximal of the expansible band 88 leading to the injection lumen 72. By fabricating the injection device 14' from a transparent plastic material, one can discern from the rise of blood in the tubular body thereof that the position sensing port 92 is located within the blood vessel 34. Those skilled in the art will appreciate that other types of sensors can be used to locate the injection ports relative to the vessel wall. For example, the obturator may have radially spaced electrodes on an exterior surface thereof with the electrodes being electrically connected to an impedance sensing instrument for detecting the change in impedance between the spaced electrodes when located in the blood stream within a blood vessel and when located in the tissue exterior to the blood vessel. As another alternative, a suitable, miniaturized pressure sensor can be disposed relative to the position sensing port 92 to reflect the pressure change encountered upon entering and/or leaving the interior of the blood vessel 34.

The injection lumen 72 is also in fluid communication with a plurality of ejection ports, as at 94, that extend through the side wall of the obturator at a location proximal of the position sensing port 92 and approximately 8-10 cm from the closed distal end 70.

The apparatus illustrated in FIG. 4 works as follows. At the conclusion of the intravascular procedure where a catheter had been introduced using the Seldinger technique, the working catheter, any guide catheter and the guidewire are stripped out of the introducer sheath 12' with the introducer sheath being left in place as illustrated in FIG. 4. The hemostatic seal 26' prevents any significant blood loss through the introducer. Next, the obturator 14', constructed in accordance with the present invention is inserted through the seal 26' and down the bore or lumen 44' of the introducer. The hemostatic seal 26' conforms closely to the outside wall surface of the obturator 14' to prevent blood loss. As the obturator is slowly advanced in the distal direction and with the balloon 90 uninflated, a point is reached where the position sensing port 92 enters the blood vessel 34 resulting in a flash of blood rising up the injection lumen 72 of the obturator which is visible to the physician. The physician now knows that the distal end portion of the obturator is disposed within the blood vessel.

At this point, the physician may assemble the syringe 80 to the hub 76 of the obturator and while holding that assembly fixed in space, he/she slides the introducer sheath 12' in the proximal direction along the exterior surface of the injection device 14 until the distal end 20' of the introducer sheath no longer penetrates the skin layer 28. Now, by slowing retracting the obturator 14' in a proximal direction a short distance, the position sensing port 92 will ultimately be located outside of the blood vessel, but will still remain in the subdermal tissue. Now, assuming the obturator is designed to incorporate a retention balloon 90, by introducing a fluid, such as normal saline under pressure into the inflation lumen 74, via tubing 84, the elastomeric band 88 will expand to form balloon 90 to assist in anchoring the obturator in place as a hemostatic agent is forced out of the syringe 80 and through the injection lumen 72 and out through the sensing port 92 and the ejection ports 94 to effectively fill the volume of the wound with a viscous blend of a hemostatic agent and a matrix for holding same. The physician may then deflate the balloon 90 and withdraw the obturator from the wound, leaving the hemostatic material in place in the wound to promote and effect hemostasis. Again, normal arterial blood pressure can be relied upon to prevent the hemostatic agent from entering the blood vessel upon removal of the obturator.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A device for sealing percutaneous punctures in a blood vessel, comprising:
   (a) an elongated tubular member having a proximal end, an outwardly flared distal end portion and a working lumen extending therebetween, the elongated tubular member further including an injection lumen leading to at least one injection outlet port in the flared distal end portion; and (b) a hub affixed to the proximal end of the elongated tubular member, the hub having an injection inlet port in fluid communication with the injection lumen adapted to transport a fluid hemostatic agent to said at least one injection outlet port and a bore aligned with the working lumen, with the bore and the working lumen dimensioned to receive a tubular vascular introducer sheath therethrough with the tubular introducer sheath being slidable relative to the elongated tubular member.

2. The device as in claim 1 wherein the flared distal end portion of the tubular member is shaped to facilitate entrance into dermal tissue when made to slide distally with respect to the tubular introducer.

3. The device as in any one of claims 1 and 2 and further including means for injecting a hemostatic agent into the injection lumen such that the hemostatic agent exits the injection outlet port.

4. The device as in claim 3 wherein the hemostatic agent is selected from the class consisting of thrombin, fibrin, fibrin glue, methacrylates, cyanoacrylates, collagen, platelet agonists, and vasoconstrictor drugs.

5. The device as in claim 4 wherein the vasoconstrictor drugs are selected from the group consisting of phenylephrine, norepinephrine, epinephrine, prostaglandin F2 alpha, endothelin, methergine, oxytocin and isoprel.

6. An apparatus for sealing percutaneous punctures in a blood vessel following a catheterization procedure, comprising in combination:

(a) a tubular introducer sheath having a distal end insertable into a wound resulting from percutaneous puncture of a blood vessel wall;

(b) a hemostatic agent injection device including a tubular member concentrically surrounding the tubular introducer sheath and slidable therealong, the injection device having a proximal hemostatic agent inlet port and a distal hemostatic agent ejection port and a lumen extending between the inlet port and the outlet port; and (c) means for injecting the hemostatic agent, under pressure, into the inlet port following placement of the ejection port within the dermal layer surrounding the tubular introducer sheath.

7. The apparatus as in claim 6 wherein the hemostatic agent is selected from the class consisting thrombin, fibrin, fibrin glue, methacrylates, cyanoacrylates, collagen, platelet agonists, and vasoconstrictor drugs.

8. The apparatus as in claim 7 wherein the vasoconstrictor drugs are selected from the group consisting of phenylephrine, norepinephrine, epinephrine, prostaglandin F2 alpha, endothelin, methergine, oxytocin and isoprel.

9. An apparatus for sealing percutaneous punctures in a blood vessel following a catheterization procedure comprising, in combination:

(a) a tubular introducer sheath having a proximal end, a distal end and a lumen extending from the proximal end to the distal end, the distal end of the introducer sheath being insertable into a wound resulting from percutaneous puncture of a blood vessel wall and adapted to facilitate insertion of a working catheter into the blood vessel;

(b) a hemostatic agent injection device including a generally rigid tubular member concentrically located relative to the tubular introducer sheath, the device having an open proximal end and a lumen leading to a closed, tapered, distal end, with a side port leading to the lumen a predetermined distance proximal of the closed, tapered distal end;

(c) means on the injection device for sensing whether the side port is disposed within or outside of the blood vessel; and (d) means for injecting a hemostatic agent through the lumen of the injection device after removal of the tubular introducer.

10. The apparatus of claim 9 and further including a plurality of additional side ports in the injection device leading to the lumen thereof.

11. The apparatus as in claim 9 wherein the means for sensing comprises an arterial blood pressure sensing means.

12. The apparatus as in claim 9 and further including a second lumen leading to an inflation port in a side wall of the injection device located distal to said side port and an inflatable balloon member affixed to the injection device and spanning the inflation port; and means for introducing and extracting an inflation fluid into and from the second lumen.

13. An apparatus for sealing percutaneous puncture wounds in a blood vessel, comprising, in combination:

(a) a tubular introducer sheath having a proximal end, a distal end and a lumen extending therebetween, a distal end portion of the tubular introducer sheath adapted for placement through a patient's dermal layer and through the puncture wound in the blood vessel to facilitate placement of instruments within the patient's vascular system;

(b) a tubular hemostatic agent injection means having an inlet port and an outlet port with a lumen extending therebetween, the outlet port being located in a side wall of the injection means a fixed, predetermined distance proximal of a closed distal end, the injection means cooperating with the tubular introducer sheath as a guide;

(c) the injection means including indicator means for establishing when the outlet port is located in the dermal layer but external to the blood vessel; and (d) means coupled to the hemostatic agent injection means for introducing a hemostatic agent under pressure at the inlet port.

14. The apparatus as in claim 13 wherein the tubular hemostatic agent injection means includes a second lumen of a size to accept the tubular introducer sheath therein, the tubular hemostatic agent injection means being slidable about the tubular introducer sheath.

15. The apparatus as in claim 13 wherein the tubular hemostatic introducer comprises an obturator sized to slide within the lumen of the tubular introducer sheath.

16. The apparatus as in claim 15 wherein the obturator includes an expansible balloon member affixed to an exterior surface of the obturator at a location distal of the outlet port, the balloon, when inflated, preventing entrance of the outlet port into the patient's blood vessel.

17. The apparatus as in claim 13 wherein the indicator means comprises an arterial blood pressure sensing device.

18. The apparatus as any of claims 9–15 and 17 wherein the hemostatic agent is a member of the class consisting of thrombin, fibrin, fibrin glue, methacrylates, cyanoacrylates, collagen, platelet agonists, and vasoconstrictor drugs.

19. The apparatus as in claim 18 wherein the vasoconstrictor drugs are selected from the group consisting of phenylephrine, norepinephrine, epinephrine, prostaglandin F2 alpha, endothelin, methergine, oxytocin and isoprel.

* * * * *